US006448475B1

(12) United States Patent
DellaPenna et al.

(10) Patent No.: US 6,448,475 B1
(45) Date of Patent: Sep. 10, 2002

(54) MANIPULATION OF TOCOPHEROL LEVELS IN TRANSGENIC PLANTS BY TRANSFORMATION WITH A SYNECHOCYSTIS 2-METHYL-6-PHYTYLPLASTOQUINOL/2-METHYL-6-SOLANYLPLASTOQUINOL-9 METHYLTRANSFERASE

(75) Inventors: Dean DellaPenna, Williamston, MI (US); David K. Shintani, Reno, NV (US)

(73) Assignee: The University and Community College System of Nevada, Reno, NV (US)

( * ) Notice: Subject to any disclaimer, the term of this patent is extended or adjusted under 35 U.S.C. 154(b) by 0 days.

(21) Appl. No.: 09/382,906

(22) Filed: Aug. 25, 1999

Related U.S. Application Data

(60) Provisional application No. 60/097,863, filed on Aug. 25, 1998.

(51) Int. Cl.[7] .............................. A01H 5/00; A01H 5/10; C12N 15/82
(52) U.S. Cl. ...................................... 800/298; 435/320.1
(58) Field of Search .............................. 435/69.1, 320.1, 435/419, 468; 536/23.2, 23.6, 23.7; 800/278, 298

(56) References Cited

PUBLICATIONS

Koziel, M. G. et al., "Optimizing expression of transgenes with an emphasis on post–transcriptional events." 1996, Plant Molecular Biology, vol. 32, pp. 393–405.*
Stam, M. et al., "The Silence of Genes in Transgenic Plants." 1997, Annals of Botany, vol. 79, pp. 3–12.*
Camara, et al., Enzymological Characterization of S–Adenosylmethionine δ–Tocopherol Methyltransferase From Capsicum Chromoplasts, Abstract from Supplement to Plant Physiology Apr. 1975, vol. 77, p. 48.
d'Harlingue et al., "Plastid Enzymes of Terpenoid Biosynthesis," *The Journal of Biological Chemistry* 260:15200–15023 (1985).
Fillatti et al., "Efficient Transfer of a Glyphosate Tolerance Gene into Tomato Using a Binary *Agrobacterium tumefaciens* Vector" *Bio/Technology* 5:726–730 (1987).
Hess, John L., "Vitamin E, α–Tocopherol," *Antioxidants in Higher Plants*, 111–134 (1993).
Ishiko et al., "Some Properties of γ–Tocopherol Methyltransferase Solubilized from Spinach Chloroplasts," *Phytochemistry* 31:1499–1500 (1992).
Michalowski et al., "Preliminary Characterization of S–adenosylmethionine: tocopherol methyltransferase from chloroplasts of *Calendula officinalis* seelings," *Acta Biochimica Polonica* 40:116–119 (1993).
Mullineaux et al., "Opportunities for the genetic manipulation of antioxidants in plant foods," *Bioactive Components of Food* (1996).
Shigeoka et al., Isolation and properties of γ–tocopherol methyltransferase in *Euglena gracilis*, *Biochimica et Biophysica Acta* 1128:220–226 (1992).
Smith et al., "Antisense RNA inhibition of polygalacturonase gene expression in transgenic tomatoes," *Letters to Nature* 334:724–726(1988).
Soll et al., "Localization and Synthesis of Prenylquinones in Isolated Outer and Inner Envelope Membranes from Spinach Chloroplasts," *Archives of Biochemistry and Biophysics* 238:290–299 (1985).

* cited by examiner

*Primary Examiner*—Amy J. Nelson
*Assistant Examiner*—Russell Kallis
(74) *Attorney, Agent, or Firm*—Quarles & Brady LLP

(57) ABSTRACT

Disclosed is a gene sequence which has been identified as encoding 2-methyl-6-phytylplastoquinol/2-methyl-6-solanylplastoquinol-9 methyltransferase from synechoeystis. By introducing a genetic construct having a 2-methyl-6-phytylplastoquinol/2-methyl-6-solanylplastoquinol-9 methyltransferase coding sequence placed under the control of a plant promoter into a plant, transgenic plants can be made having altered 2-methyl-6-phytylplastoquinol/2-methyl-6-solanylplastoquinol-9 methyltransferase expression, to effect changes in the tocopherol profile of the plant. Transgenic plants can be made that have altered tocopherol levels in their tissues.

7 Claims, 5 Drawing Sheets

General Tocopherol Structure

General Tocotrienol Structure

| Form | $R_1$ | $R_2$ |
|---|---|---|
| α-tocopherol/trienol | -CH₃ | -CH₃ |
| β-tocopherol/trienol | -CH₃ | -H |
| γ-tocopherol/trienol | -H | -CH₃ |
| δ-tocopherol/trienol | -H | -H |

MANIPULATION OF TOCOPHEROL LEVELS IN TRANSGENIC PLANTS BY TRANSFORMATION WITH A SYNECHOCYSTIS 2-METHYL-6-PHYTYLPLASTOQUINOL/2-METHYL-6-SOLANYLPLASTOQUINOL-9 METHYLTRANSFERASE

CROSS-REFERENCE TO RELATED APPLICATIONS

This application claims priority to U.S. Provisional Application Serial No. 60/097,863 filed Aug. 25, 1998.

STATEMENT REGARDING FEDERALLY SPONSORED RESEARCH OR DEVELOPMENT

Not applicable.

BACKGROUND OF THE INVENTION

Vitamin E is an essential component of mammalian diets. Epidemiological evidence indicates that Vitamin E supplementation results in decreased risk for cardiovascular disease and cancer, aids in immune function, and generally prevents or slows a number of degenerative disease processes in humans (Traber and Sies, *Annu. Rev. Nutr.* 16:321–347, 1996). Vitamin E functions in stabilizing the lipid bilayer of biological membranes (Skrypin and Kagan, *Biochim. Biophys. Acta* 815:209 1995; Kagan, *N.Y. Acad. Sci.* p 121, 1989; Gomez-Fernandez et al., *Ann. N.Y. Acad. Sci.* p 109, 1989), reducing polyunsaturated fatty acid (PUFA) free radicals generated by lipid oxidation (Fukuzawa et al., *Lipids* 17: 511–513, 1982), and quenching singlet oxygen species (Fryer, *Plant Cell Environ.* 15(4):381–392, 1992).

Vitamin E, or α-tocopherol, belongs to a class of lipid-soluble antioxidants that includes α, β, γ, and δ-tocopherols and α, β, γ, and δ-tocotrienols, and related compounds known as plastoquinones. Although α, β, γ, and δ-tocopherols and α, β, γ, and δ-tocotrienols are sometimes referred to collectively as "Vitamin E" in the popular press, Vitamin E is properly defined chemically solely as α-tocopherol. Of the various tocopherols present in foodstuff, α-tocopherol is the most significant for human health both because it is the most bioactive of the tocopherols and also because it is the tocopherol most readily absorbed and retained by the body (Traber and Sies, *Annu. Rev. Nutr.* 16:321–347, 1996). The in vivo antioxidant activity of α-tocopherol is higher than the antioxidant activities of β, γ, and δ-tocopherol (Kamal-Eldin and Appelqzvist *Lipids* 31:671–701, 1996).

Only plants and certain other photosynthetic organisms, including cyanobacteria, synthesize tocopherols. Therefore, dietary tocopherols are obtained almost exclusively from plants. Plant tissues vary considerably in total tocopherol content and tocopherol composition. The predominant tocopherol in green, photosynthetic plant tissues is α-tocopherol. Leaf tissue can contain from 10–50 μg total tocopherols/gram fresh weight.

Non-green plant tissues and organs exhibit a wider range of both total tocopherol levels and tocopherol compositions. In general, most of the major food staple crops (e.g., rice, corn, wheat, potato) produce low to extremely low levels of total tocopherols, of which only a small percentage is α-tocopherol (Hess, Vitamin E, α-tocopherol, In Antioxidants in Higher Plants, R. Alscher and J. Hess, Eds. 1993, CRC Press, Boca Raton. pp 111–134). Oil seed crops generally contain much higher levels of total tocopherols; however, α-tocopherol is present only as a minor component and β, γ, and δ-tocopherols predominate (Taylor and Barnes, *Chemy Ind.*, Oct.:722–726, 1981).

Daily dietary intake of 15–30 mg of vitamin E is recommended to obtain optimal plasma α-tocopherol levels. It is quite difficult to achieve this level of vitamin E intake from the average American diet. For example, one could obtain the recommended daily allowance of Vitamin E by daily consumption of over 750 grams of spinach leaves (in which α-tocopherol comprises 60% of total tocopherols) or 200–400 grams of soybean oil.

One alternative to relying on diet alone to obtain the recommended levels of vitamin E is to take a vitamin E supplement. However, most vitamin E supplements are synthetic vitamin E having six stereoisomers, whereas natural vitamin E vitamin is a single isomer. Furthermore, supplements tend to be relatively expensive, and the general population is disinclined to take vitamin supplements on a regular basis.

Although tocopherol function in plants has been less extensively studied than tocopherol function in mammalian systems, it is likely that the analogous functions performed by tocopherols in animals also occur in plants. In general, plant tocopherol levels have been found to increase with increases in various stresses, especially oxidative stress. Increased α-tocopherol levels in crops are associated with enhanced stability and extended shelf life of fresh and processed plant products (Peterson, *Cereal-Chem* 72(1):21–24, 1995; Ball, *Fat-soluble vitamin assays in food analysis. A comprehensive review.* London: Elsevier Science Publishers LTD, 1988).

Vitamin E supplementation of swine, beef, and poultry feeds has been shown to significantly increase meat quality and extend the shelf life of post-processed meat products by retarding post-processing lipid oxidation, which contributes to the formation of undesirable flavor components (Ball, supra 1988; Sante and Lacourt, *J. Sci. Food Agric.* 65(4):503–507, 1994; Buckley et al., *J. of Animal Science* 73:3122–3130, 1995).

The related compounds plastoquinone (sometimes referred to here as PQ) and the tocopherols are the most abundant quinones produced in the plastids of plant cells. These compounds are synthesized in a common pathway, which is illustrated in FIG. 1. PQ is an important component of the chloroplast photosynthetic electron transport chain and accounts for as much as 50% of the total quinone levels in the plastids of plant cells. As can be appreciated from the synthetic pathway, the levels of PQ and tocopherols are related by the enzymes which catalyze the production of the precursors of both classes of compounds.

SUMMARY OF THE INVENTION

The present invention is based on an isolated DNA fragment including a coding sequence for a 2-methyl-6-phytylplastoquinol/2 methyl-6-solanylplastoquinol-9 methyltransferase in a transgenic plant.

The invention is also a heterologous genetic construct comprising a 2-methyl-6-phytylplastoquinol/2-methyl-6-solanylplastoquinol-9 methyltransferase coding sequence operably connected to a plant, bacterial, or fungal promoter not natively associated with the coding sequence.

Another aspect of the present invention is a method of altering the tocopherol profile of a plant comprising the steps of: (a) providing a heterologous genetic construct comprising a 2-methyl-6-phytylplastoquinol/2-methyl-6- solanylplastoquinol-9 methyltransferase coding sequence operably connected to a plant promoter not natively associated with the coding sequence; and (b) introducing the construct into the genome of a plant.

The present invention is also directed toward transgenic plants which have an altered ratio of δ-tocopherol to γ-tocopherol and α-tocopherol to β-tocopherol, thus increasing the nutritive value of the plants and products therefrom for human and animals.

In another embodiment, the invention is a plant comprising in its genome a heterologous genetic construct comprising a 2-methyl-6-phytylplastoquinol/2-methyl-6-solanylplastoquinol-9 methyltransferase coding sequence operably connected to a promoter that is functional in plants.

It is an object of this invention to provide a plant having an altered δ-tocopherol to γ-tocopherol ratio.

Other objects, features, and advantages of the invention will become apparent upon review of the specification and claims.

DETAILED DESCRIPTION OF THE INVENTION

The present invention is, in part, directed to a plant comprising in its genome a genetic construct comprising a 2-methyl-6-phytylplastoquinol/2-methyl-6-solanylplastoquinol-9 methyltransferase coding sequence operably connected to a plant promoter not natively associated with the coding sequence. Such transgenic plants exhibit altered levels of tocopherols and plastoquinols relative to the wild type plants of the same species. Just for the sake of ease of nomenclature, this enzyme will sometimes be referred to here as methyl transferase 1.

Figure 1:
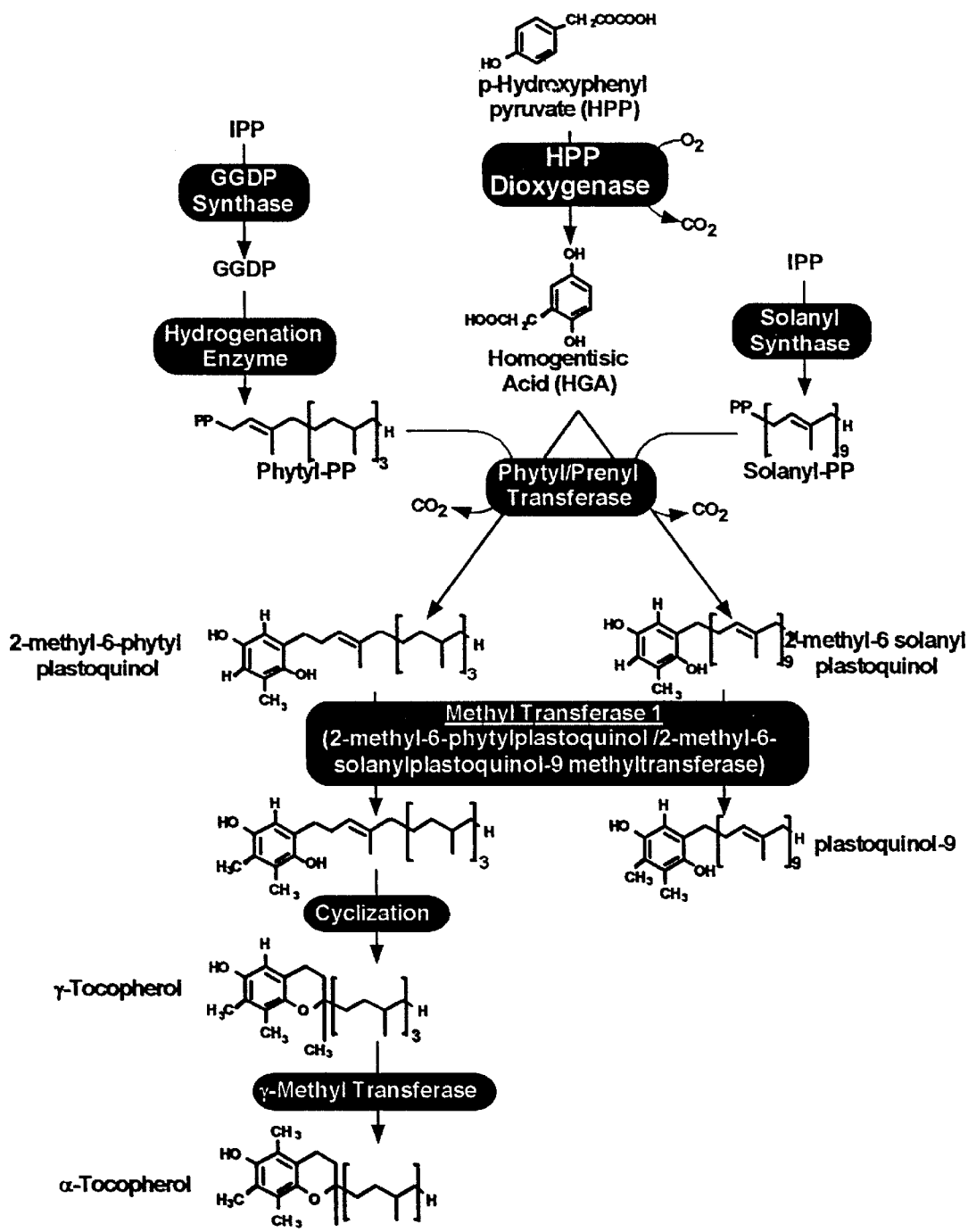
FIG. 1 is an illustration of the pathway of biosynthesis of tocopherols and plastoquinols.
Figure 2:
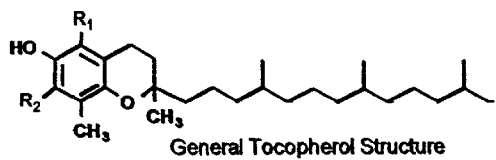
FIG. 2 is an illustration of the general molecular structures of tocopherols and plastoquinols.
Figure 2:
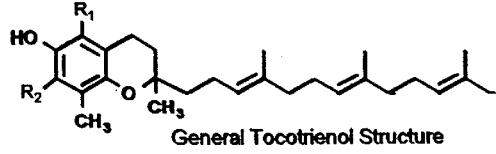
Figure 2:
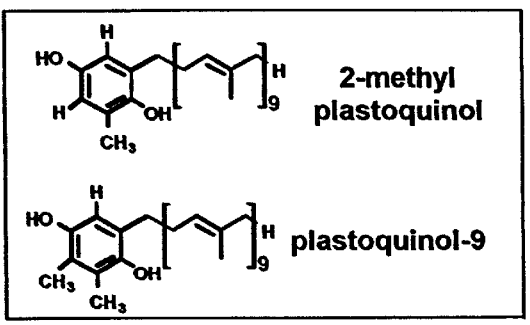

Tocopherols and plastoquinones, the most abundant quinones in plant plastids, are synthesized by a common pathway (Hess, *Antioxidants in Higher Plants*, CRC Press: Boca Raton p 140–152, 1993; Soll, *Plant Cell Membranes*, Academic Press: San Diego p 383–392, 1987). The synthesis of tocopherols involves four steps catalyzed by at least six enzymatic activities. A portion of that pathway is illustrated in FIG. 1. The synthesis of tocopherols can be broken into four steps involving a minimum of six enzymatic activities.

The first step is the synthesis of the homogentisic acid head group. The head group for both tocopherols and plastoquinones, homogentisic acid (HGA), is produced from p-hydroxyphenylpyruvic acid (HPP) by the enzyme p-hydroxyphenylpyruvic acid dioxygenase (HPPDase).

The second step is the addition of the hydrophobic tail to generate 2-methyl-6-phytylplastoquinol. HGA is subject to phytylation/prenylation (phytyl and solanyl, $C_{20}$ and $C_{45}$, respectively) coupled to a simultaneous decarboxylation to form the first true tocopherol and plastoquinone intermediates, 2-methyl-6-phytylplastoquinol and 2-methyl-6-solanylplastoquinol-9, respectively. This step of the pathway is the branchpoint for commitment of carbon to either tocopherols/tocotrienols or plastoquinones.

Steps three through five involve methylations and ring cyclization to generate the full suite of tocopherols and plastoquinols. The 2-methyl-6-phytylplastoquinol generated by addition of phytol-PP to HGA (or GGDP addition for tocotrienols) is the common intermediate in the synthesis of all tocopherols. The next steps in tocopherol synthesis are ring methylations and cyclization. The preferred sequence of these reactions for α-tocopherol synthesis in isolated spinach chloroplasts is 1) ring methylation at position 3 on 2-methyl-6-phytylplastoquinol, to yield 2,3-dimethyl-6-phytylplastoquinol or methylation at position 3 on 2-methyl-6-solanylplastoquinol-9, to yield plastoquinol-9, 2) cyclization to yield δ-tocopherol and, finally, 3) a second ring methylation at position 5 to yield α-tocopherol (20). The first ring methylation reaction is common to both tocopherol and plastoquinone synthesis and is carried out by a single enzyme, 2-methyl-6-phytylplastoquinol/2-methyl-6-solanylplastoquinol-9 methyltransferase, of methyl transferase 1. This enzyme specifically methylates the 3 position of the aromatic head group of 6-methyl-6-phytylplastoquinol and 2-methyl-6-solanylplastoquinol. Evidence supporting a common first methylation enzyme comes from a mutant in maize that is disrupted in methylation at position 3 of tocopherol and plastoquinone synthesis and accumulates 2-methyl-6-solanylplastoquinol-9 and β-tocopherol (21, DellaPenna and Shintani, unpublished). The second ring methylation enzyme (δ-tocopherol methyltransferase) is a distinct enzymatic activity from the first methyltransferase has been purified from plants (22, 23). The first methyltransferase, 2-methyl-6-phytylplastoquinol/2-methyl-6-solanylplastoquinol-9 methyltransferase, is the enzyme that has been cloned and functionally characterized in Synechocystis and the molecular manipulation of which in plants is described here.

While steps one and two discussed above are likely to be critical for regulating the total amount of tocopherols synthesized in a tissue, the methylation enzymes are involved primarily in regulating the final composition of the tocopherol pool. Data obtained from mutant studies in sunflower suggest that although the enzymes catalyzing the methylation of the aromatic head group have a high degree of influence over tocopherol composition, the genetic manipulation of these enzyme activities do not affect the overall regulation of tocopherol content (24). Normally, the seed tocopherol composition in cultivated sunflower (*Helianthus annuus L.*) is primarily α-tocopherol (i.e. 95–100% of the total tocopherol pool) (25). However, two mutant sunflower lines have been identified with tocopherol compositions of 95% δ-tocopherol/5% α-tocopherol and 50% β-tocopherol/50% α-tocopherol, respectively. Although these presumed tocopherol methylation mutants showed drastic alterations in their tocopherol profiles in seed, their overall total tocopherol levels do not differ significantly from that of wild type sunflower (24). These results indicate that it should be possible to alter the tocopherol profile of different crop species by manipulating 2-methyl-6-phytylplastoquinol/2-methyl-6-solanylplastoquinol-9 methyltransferase without having a detrimental effect on the total tocopherol pool size in the target tissues.

This disclosure provides a scientific basis for molecular manipulation of the tocopherol composition in a wide variety agricultural crops and plant tissues via manipulation of 2-methyl-6-phytylplastoquinol/2-methyl-6-solanylplastoquinol-9 methyltransferase individually or in combination with the recently cloned δ-tocopherol methyltransferase enzyme. We have isolated a gene from the photosynthetic bacteria Synechocystis encoding the enzyme 2-methyl-6-phytylplastoquinol/2-methyl-6-solanylplastoquinol-9 methyltransferase (methyltransferase 1) that is required for the first methylation step of tocopherol synthesis and the only methylation step of plastoquinone synthesis. Functional analysis of this gene by gene disruption in Synechocystis and in vitro 2-methyl-6-phytylplastoquinol/2-methyl-6-solanylplastoquinol-9 methyltransferase activity of the *E. coli* expressed Synechocystis 2-methyl-6-phytylplastoquinol/2-methyl-6-solanylplastoquinol-9 methyltransferase gene conclusively defined the activity of the encoded protein as 2-methyl-6-phytylplastoquinol/2-methyl-6-solanylplastoquinol-9 methyltransferase. Overexpression of the protein encoded by this gene in plants, or a homologous gene isolated from plants, will allow conversion of β-tocopherol to α-tocopherol and δ-tocopherol to δ-tocopherol in any tissue that contains these substrates. Antisense inhibition of expression of the plant gene encoding this enzyme activity will result in b-tocopherol accumulation at the expense of α-tocopherol and δ-tocopherol accumulation at the expense of δ-tocopherol. Although both methylation reactions described earlier are essential for α-tocopherol synthesis, 2-methyl-6-phytylplastoquinol/2-methyl-6-solanylplastoquinol-9 methyltransferase regulates the ratio of δ to γ- and β- to α-forms of tocopherols and tocotrienols in most plant tissues. Increasing 2-methyl-6-phytylplastoquinol/2-methyl-6-solanylplastoquinol-9 methyltransferase activity will decrease the ratio of these tocopherols while inhibiting expression will increase the ratios of these tocopherols.

As demonstrated in the examples and other data presented below, the seeds of plants transformed with a genetic construct comprising a methyltransferase 1 gene under the control of either the seed specific promoter or the constitutive promoter exhibit a dramatic increase in the ratio of δ-tocopherol:γ-tocopherol. It is possible to catalyze essentially all of the δ-tocopherol in a given plant tissue to γ-tocopherol by expressing a methyltransferase 1 gene in that plant tissue.

Isolation and functional analysis of the 2-methyl-6-phytylplastoquinol/2-methyl-6-solanylplastoquinol-9 methyltransferase gene from Synechocystis PCC6803 was accomplished by concurrently pursuing the complementary molecular genetic approaches described in detail in the examples. These same techniques may be used to probe the genomes of other species to obtain the homologous genes in those other species. It has already been demonstrated that Synechocystis and the model plant species Arabidopsis synthesize tocopherols by similar or identical pathways and both are highly tractable genetic, molecular, and biochemical systems.

The DNA sequence of the 2-methyl-6-phytylplastoquinol/ 2-methyl-6-solanylplastoquinol-9 methyltransferase genes from Synechocystis PCC6803 is shown in SEQ ID NO:1. The corresponding deduced amino acid sequences of the protein is shown in SEQ ID NO: 2.

It is expected that the present invention may be practiced using a 2-methyl-6-phytylplastoquinol/2-methyl-6-solanylplastoquinol-9 methyltransferase gene from any photosynthetic organism. It is well within the ability of one of skill in the art to isolate a plant 2-methyl-6-phytylplastoquinol/2-methyl-6-solanylplastoquinol-9 methyltransferase gene using the sequences disclosed herein. The sequence can be used to screen public computer databases of plant cDNAs (dbEST databases) and genomic sequences. Alternatively, the sequences could be used to design probes for use in identifying genomic or cDNA clones containing a 2-methyl-6-phytylplastoquinol/2-methyl-6-solanylplastoquinol-9 methyltransferase sequence. Another approach would be to use the sequences to design oligonucleotide primers for use in PCR amplification of 2-methyl-6-phytylplastoquinol/2-methyl-6-solanylplastoquinol-9 methyltransferase genes from plant DNA.

To determine whether one has identified a 2-methyl-6-phytylplastoquinol/2-methyl-6-solanylplastoquinol-9 methyltransferase sequence, one could perform a gene replacement study using wild type Synechocystis, a complementation study using a Synechocystis knockout mutant, or an in vitro enzyme assay using a suitable substrate and 2-methyl-6-phytylplastoquinol/2-methyl-6-solanylplastoquinol-9 methyltransferase protein expressed in *E. coli* or another suitable expression system. One example of such a test in *E. coli* is described below. A genetic construct comprising the 2-methyl-6-phytylplastoquinol/2-methyl-6-solanylplastoquinol-9 methyltransferase coding sequence operably connected to a plant promoter can be constructed and used to transform Arabidopsis or a plant or crop plant of interest. A transgenic plant comprising the construct in its genome would be expected to have altered expression of 2-methyl-6-phytylplastoquinol/ 2-methyl-6-solanylplastoquinol-9 methyltransferase and an altered tocopherol profile relative to an untransformed, wild-type plant. It is expected that polyploid plants having more than one copy of the 2-methyl-6-phytylplastoquinol/2-methyl-6-solanylplastoquinol-9 methyltransferase gene may have allelic variations among γ-tocopherol methyltransferase gene sequences. It is anticipated that putative 2-methyl-6-phytylplastoquinol/2-methyl-6-solanylplastoquinol-9 methyltransferase gene sequences having less than 100% homology to SEQ ID NO: 1 encode proteins having 2-methyl-6-phytylplastoquinol/2-methyl-6-solanylplastoquinol-9 methyltransferase activity.

It is envisioned that minor sequence variations from SEQ NO:1 associated with nucleotide additions, deletions, and mutations, whether naturally occurring or introduced in vitro, will not affect methyltransferase 1 activity. The scope of the present invention is intended to encompass minor variations in methyltransferase 1 sequences. Also, it is now well within the level of ordinary skill in the art of plant genetic engineering to alter the coding sequence for a gene by changing codons specifying for common amino acids or by making conservative amino acid substitutions at DNA sequences encoding non-critical portions of enzymes.

Construction of an expression vector comprising a 2-methyl-6-phytylplastoquinol/2-methyl-6-solanylplastoquinol-9 methyltransferase coding sequence operably connected to a plant promoter not natively associated with the coding sequence will be achieved using standard molecular biology techniques known to the art. The plant promoter may be a tissue-specific promoter such as a seed-specific promoter (e.g., napin or DC3), a constitutive promoter such as CaMV 35S, a developmental stage-specific promoter, or an inducible promoter. Promoters may also contain certain enhancer sequence elements that improve efficiency of transcription. Optionally, the construct may contain a termination signal, such as the nopaline synthase terminator (NOS). Preferably, the constructs will include a selectable or screenable marker to facilitate identification of transformants. The constructs may have the coding region in the sense or antisense orientation.

Once a genetic construct comprising a 2-methyl-6-phytylplastoquinol/2-methyl-6-solanylplastoquinol-9 methyltransferase gene has been obtained, it can readily be introduced into a plant or plant tissue using standard methods known to the art. For example, the Agrobacterium transformation system is known to work well with all dicot plants and some monocots. Other methods of transformation equally useful in dicots and monocots may also be used. Transgenic plants may be obtained by particle bombardment, electroporation, or by any other method of transformation known to one skilled in the art of plant molecular biology. The experience to date in the technology of plant genetic engineering has taught that the method of gene introduction does not affect the phenotype achieved in the transgenic plants.

A transgenic plant may be obtained directly by transformation of a plant cell in culture, followed by regeneration of a plant. More practically, transgenic plants may be obtained from transgenic seeds set by parental transgenic plants. Transgenic plants pass on inserted genes, sometimes referred to as transgenes, to their progeny by normal Mendelian inheritance just as they do their native genes. Methods for breeding and regenerating plants of agronomic interest are known to the art. Experience with transgenic plants has also demonstrated that the inserted gene, or transgene, can be readily transferred by conventional plant breeding techniques into any desired genetic background.

Set forth in Table 2 below is a listing of relative abundance of tocopherol species in common crop plants and vegetables. In the center column of that table is the tocopherol levels and relative abundance as they occur in these plants today. Shown in the right-hand column of that table is the relative abundance of these tocopherols that can be achieved by the expression in these plants of an effective heterologous methyltransferase 1. The effect on the proportion of species of tocopherol present is striking for some plants and modest for others, depending on the tocopherol profile of the native plant. If one combines the availability of the methyltransferase 1 gene with the availability of the γ-tocopherol methyltransferase gene described previously, it becomes possible to direct total tocopherol production in a plant species to α-tocopherol, if that is desired.

It is reasonable to expect that the expression of heterologous methyltransferase 1 in a transgenic plant will result in alterations in the tocopherol profile in that plant. In addition to the inherent advantage of increasing the δ-tocopherol:γ-tocopherol ratio, changes in the tocopherol profile may result in unique, advantageous phenotypes. This invention is intended to encompass other advantageous phenotypes that may result from alterations in tocopherol biosynthesis in plants obtained by the practice of this invention.

Using the information disclosed in this application and standard methods known to the art, one of skill in the art could practice this invention using any crop plant or forage plant of interest.

The following nonlimiting examples are intended to be purely illustrative. It is also understood that the present invention is not limited to the exemplified embodiment or practice of the examples set forth below, but is intended to encompass all such modifications and variations as come within the scope of the claims which follow.

EXAMPLES

Arabidopsis and Synechocystis as Complementary Model Systems for Studying and Manipulating Tocopherol Biosynthesis in Plants Isolation and functional analysis of the Synechocystis 2-methyl-6-phytylplastoquinol/2-methyl-6-solanylplastoquinol-9 methyltransferase was accomplished by concurrently pursuing complementary molecular genetic approaches in *Arabidopsis thaliana* and Synechocystis strain PCC6803. These two model organisms were selected because both synthesize tocopherols by identical pathways and both are highly tractable genetic, molecular and biochemical systems. Many reactions and pathways are similar in the two organisms, the most relevant to this patent being similarities in the synthesis of tocopherols. The ease with which gene disruption (26) can be used to test gene function in Synechocystis combined with the recent report of the complete Synechocystis genome sequence (27) make it an excellent model system for isolation of tocopherol pathway enzymes and as a rapid test organism for functional analysis of plant derived cDNAs involved in tocopherol synthesis. Likewise, Arabidopsis genes of the pathway that have been identified and cloned in by the inventors here have proven instrumental for isolating homologs from Synechocystis already for other genes.

Identification of a Potential Tocopherol Biosynthetic Operon in Synechocystis

Recently, the entire DNA sequence of the Synechocystis PCC6803 genome has been determined and made available in an internet accessible database (27). The inventors here have previously reported the isolation and characterization of a distinct but possibly related enzyme, δ-tocopherol methyl transferase, encoded by an ORF which was designated SLR0089. The protein sequence of SLR0089 was used as a probe to identify related genes in the Synechocystis genome database. Several ORFs were identified with an ORF designated SLL0418 showing the highest homology to SLR0089, suggesting that it might be a related tocopherol methyltransferase. SLL0418 encompasses bases 2,096,618 to 2,097,574 of the published Synechocystis database sequence. Upon further examination, SLL0418 was found to contain conserved S-adenosylmethionine (SAM) binding domains that one would expect to be present in tocopherol methyltransferase enzymes. To test the hypothesis that Synechocystis gene SLL0418 encodes 2-methyl-6-phytylplastoquinol/2-methyl-6-solanylplastoquinol-9 methyltransferase, two approaches were used to test the function of the protein encoded by the Synechocystis SLL0418 gene. The first approach involves the disruption of the SLL0418 Synechocystis gene in its native host by gene replacement techniques (26). The resulting SLL0418 mutant Synechocystis strain was then analyzed for loss of product/function, that is accumulation of tocopherol intermediates or other alterations in the normal tocopherol profile. The second approach involves the expression of the Synechocystis gene in *E. coli*, and the direct analysis of these *E. coli* strains for 2-methyl-6-phytylplastoquinol/2-methyl-6-solanylplastoquinol-9 methyltransferase activity.

Figure 3:
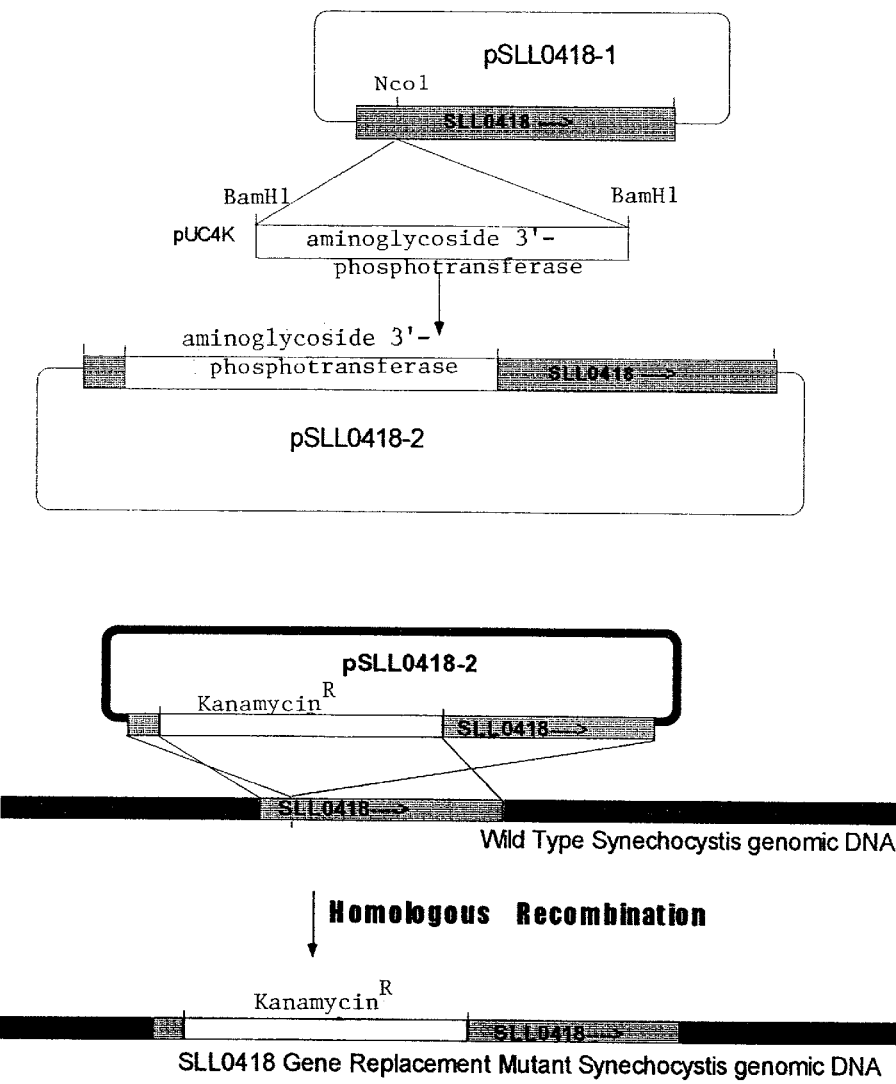
FIG. 3 is a schematic illustration of some of the molecular manipulations of DNA for the gene of interest here as described in the examples below.

The sequencing of the entire Synechocystis genome (27) has greatly facilitated the identification, isolation and functional analysis of specific genes of interest. Once targeted genes have been identified in the database, these gene sequences can be amplified from the Synechocystis genomic DNA using polymerase chain reaction (PCR). The resulting amplification product can then be cloned into an appropriate plasmid vector for either expression in *E. coli* or for use in the creation of gene disruption constructs that will be needed for Synechocystis gene replacement experiments (26). This method was used to amplify and clone the putative 2-methyl-6-phytylplastoquinol/2-methyl-6-solanylplastoquinol-9 methyltransferase gene, SLL0418, by a strategy as illustrated in FIG. 3.

PCR Amplification of Synechocystis Open Reading Frame SLL0418

The SLL0418 DNA sequence was amplified from Synechocystis PCC6803 genomic DNA by the polymerase chain reaction (PCR). Synechocystis genomic DNA was isolated as described by Williams (Methods in Enzymology (1987) 167: 766–778). PCR primers were designed from the DNA sequence corresponding to the SLL0418 open reading frame that was described on the Synechocystis Cyanobase Web-site (www.kazusa.or.jp/cyanobase/about.html). The sense-strand specific primer, designated as SLL0418F, and the non-sense-strand specific primer, designated as SLL0418R had the following sequences:

SLL0418F=5'-CATATGCCCGAGTATTTGCTTCTG-3' (SEQ ID NO:3)

SLL0418R=5'-TTTAAGCTTGAGTGGCGTTTTTTC-3' (SEQ ID NO:4)

The amplification of the SLL0418 open reading frame was done in a 100 µl reaction containing 0.4 mM dATP, 0.4 mM dGTP, 0.4 mM dCTP, 0.4 mM dTTP, 20 pmole SLL0418F primer, 20 pmole SLL0418R primer, 20 ng Synechocystis PCC6803 genomic DNA, 20 mM Tris-HCl (pH 8.4), 50 mM KCl, 2 mM $MgCl_2$, 2.5 units Pfu polymerase (Stratagene). PCR thermocycle conditions were performed as follows:

5 minutes 95° C. (1 cycle)

1 minute 95° C.→1 minute 55° C.→2 minutes 72° C. (35 cycles)

10 minutes 72° C. (1 cycle)

Sub-cloning of Amplified SLL0418 Open Reading Frame

The amplified SLL0418 open reading frame PCR product was subcloned into pBluescript KS II. The PCR reaction was purified by extraction with phenol:$CHCl_3$ (1 volume:1 volume) and subsequent ethanol precipitation. The ethanol precipitate containing the amplified SLL0418 product was resuspended in water. The cloning vector, pBluescript II KS, was digested with the restriction enzyme EcoRV. The PCR fragment and the EcoRV digested pBluescript II KS plasmid were then fractionated on a 0.7% agarose TBE gel. The PCR fragment was excised from the gel and purified using a Genesorb kit. The purified PCR fragment and the EcoRV digested pBluescript II KS were combined in a DNA ligation reaction containing 20 mM Tris-HCl (pH 7.6), 5 mM $MgCl_2$, 5 mM DTT, 50 ug/ml bovine serum albumin, 0.5 mM ATP, 50 units/ml T4 ligase, 15% polyethylene glycol. The ligation reaction was incubated over-night at room temperature. This ligation reaction was then transformed into competent E. coli DH5α cells and plated on LB medium containing 100 mg/liter ampicillin. Ampicillin resistant colonies were then isolated and plasmids were purified. The resulting plasmid, designated as pSLL0418-1, was sequenced using T7 and T3 sequencing primers to confirm the presence and orientation of the amplified SLL0418 open reading frame DNA sequence.

Construction of SLL0418 Gene Replacement Vector

Due to the ease at which it can be transformed (28, 29) and high efficiency of homologous recombination (26, 29), Synechocystis is highly amenable to molecular genetic manipulation. Gene replacement approaches in Synechocystis have been extensively and successfully used by photosynthesis researchers as a means to generated site-direct mutations in almost every gene encoding a photosystem component. The procedures for gene replacement involves the recombination of an endogenous gene with a homologous gene constructed in vitro to contain a disruption within its coding sequence. In our case, disruption was generated by the insertion of a kanamycin resistance cassette into the coding region of the PCR cloned target gene, as illustrated in FIG. 3. When the endogenous gene is successfully replaced with the gene disruption construct during transformation, the resulting recombinant Synechocystis exhibits a kanamycin resistant phenotype. Because Synechocystis is known to contain multiple copies of its genome within single cells (29), several sub-culturings of antibiotic resistant colonies on selection medium were done to ensure that all wild type genomes have been segregated away from the mutated genome. Finally, southern blot and PCR analysis were performed to confirm that the expected gene replacement event has occurred. Two independent authentic gene replacement mutants were then analyzed by HPLC for loss of product/function related to tocopherol synthesis.

The aminoglycoside 3'-phosphotransferase gene from the transposon Tn903 confers resistance to kanamycin in Synechocystis. This gene was sub-cloned from the plasmid pUC4K into a unique NcoI restriction site within the SLL0418 open reading frame in pSLL0418-1. The aminoglycoside 3'-phosphotransferase gene was cut out of pUC4K as a BamH1 fragment and the BamH1 site was filled in with Klenow enzyme to generate blunt ends. Approximately 10 µg of pUC4K was digested for 2 hours with BamH1. The digested plasmid was then purified by phenol:Chloroform extraction followed by ethanol precipitation. The resulting pellet containing the digested plasmid was then resuspended in a 50 µl solution containing 50 mM Tris-HCl (pH 7.2), 0.4 mM dCTP, 0.4 mM dGTP, 0.4 mM dATP, 0.4 mM dTTP, 10 mM $MgCl_2$, 1 mM DTT, 2 units of Klenow and incubated for 1 hour at 37° C. The sub-cloned SLL0418 plasmid construct, pSLL0418-1, was digested with Nco1. The ends of the Nco1 digested pSLL0418-1 were filled in using Klenow as described above for the BamH1 digested pUC4K plasmid. The resulting blunt ended pSLL0418-1 NcoI fragment and the blunt ended BamH1 fragment from pUC4K containing the aminoglycoside 3'-phosphotransferase gene were then isolated from a 0.7% agarose TBE gel using the Genesorb kit. These two DNA fragments were then combined to form a DNA ligation reaction containing 20 mM Tris-HCl (pH 7.6), 5 mM MgC12, 5 mM DTT, 50 ug/ml bovine serum albumin, 0.5 mM ATP, 50 units/ml T4 ligase, 15% polyethylene glycol. The ligation reaction was incubated over-night at room temperature. This ligation reaction was then transformed into competent E. coli DH5a cells and plated on LB medium containing 50 mg/liter kanamycin and 100 mg/liter ampicillin. Colonies resistant to both kanamycin and ampicillin were then isolated and plasmids were purified. The resulting plasmid was designated as pSLL0418-2.

Transformation of Synechocystis PCC6803 with the SLL0418 Gene Replacement Vector The SLL0418 gene replacement vector, pSLL0418-2, was transformed into Synechocystis PCC6803 by the method described by Williams (Methods in Enzymology (1987) 167: 766–778). Transformed Synechocystis were selected for on BG-11 medium containing 15 mM glucose and 15 mM kanamycin. All cultures were grown under continuous light at 26° C. Two independent transformants were carried through 5 sub-culturings of single colonies to fresh medium. The resulting transformed Synechocystis strains were designated as pSLL0418-2a and 2b.

Extraction of Synechocystis Lipids

Approximately 200 mg of cells were scraped from 2 week old Synechocystis cultures grown on BG-11 agar medium. The cells were homogenized in 6 ml of 2:1 (volume:volume) methanol:$CHCl_3$ containing 1 mg/ml butylated hydroxytolulene (BHT) using a polytron homogenizer. Then 2 ml of $CHCl_3$ and 3.4 ml of double-distilled water was added to the homogenate. The lower lipid phase was removed and dried under nitrogen gas. The dried lipids were resuspended in 200 ml of HPLC grade hexane containing 1 mg/ml BHT.

Tocopherol Analysis

Figure 4:
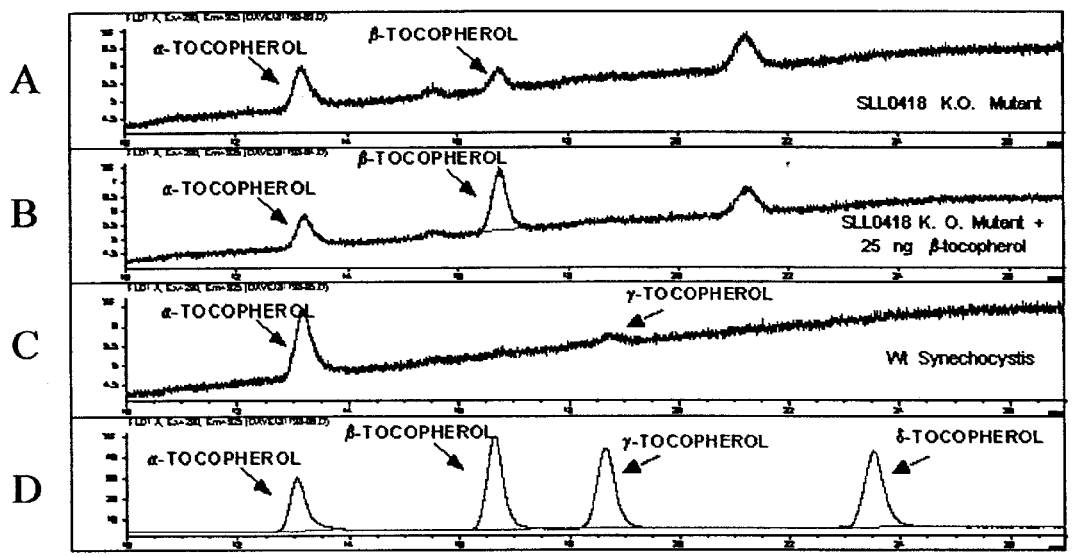
FIG. 4 illustrates the output of HPLC analysis of Synechocystis mutants described in the examples below.

Tocopherols were analyzed by HPLC using a Hewlett-Packard Series 1100 HPLC system with a fluorescence detector. For normal phase HPLC analysis of tocopherols, $CHCl_3$ extracts were dried under vacuum and the resulting lipid residue was resuspended in hexane. Tocopherols were fractionated on a Licosorb Si60A 4.6×250 mm HPLC column using a 20 minute linear gradient of 8% to 18% diisopropylether in hexane at 42° C. using a flow rate of 1 ml/minute. For normal phase analysis, tocopherols were detected by fluorescence at 325 nm after excitation at a wavelength of 290 nm. Individual tocopherol species were quantified by comparing their fluorescence signals with standard curves made from known quantities of authentic tocopherol standards. Wild-type Synechocystis produces α-tocopherol as its most abundant tocopherol, i.e. >95% of total tocopherols as can be seen in FIG. 4. In FIG. 4, the output of the HPLC column is represented for both the wild-type and the knock-out Synechocystis strains. The topmost panel, designated A, corresponds to the SLL0418 knock-out mutant, the third panel C represents the wild-type strain while the forth panel D shows the location of the peaks for the tocopherols. When SLL0418 is disrupted, Synechocystis synthesizes greatly reduced levels of α-tocopherol and instead accumulates β-tocopherol to a much greater level, as illustrated in FIG. 4, panel A. The large reduction of α-tocopherol production and consequential accumulation of β-tocopherol when production of SLL0418 is eliminated conclusively demonstrates that SLL0418 encodes 2-methyl-6-phytylplastoquinol/2-methyl-6-solanylplastoquinol-9 methyltransferase, the first methyltransferase in α-tocopherol biosynthesis and the only methyltransferase in plastoquinone synthesis.

Confirmation of SLL0418 Gene Replacement by Polymerase Chain Reaction

PCR was used to determine if homologous recombination occurred between the Synechocystis chromosome and the introduced gene replacement plasmid, pSLL0418-2a. Genomic DNA was isolated as described above from wild type Synechocystis and Synechocystis strains transformed with pSLL0418-2 (i.e. Strains pSLL0418-2a and b). PCR reactions were then performed as described above using SLL0418 specific PCR primers (i.e. the SLL0418F and SLL0418R primers described above) and genomic DNA templates isolated from wild type and pSLL0418-2a and b Synechocystis strains. Control PCR reactions were also done as described above using pSLL0418-1 and pSLL0418-2 DNAs as control templates. The resulting PCR products were fractionated on 1% agarose TBE gels and visualized after staining the gels with ethidium bromide.

Demonstration of Tocopherol Biosynthetic Enzyme Activity by Expression and Biochemical Analysis in E. coli/Expression of SLL0418 Gene in E. coli A second approach to characterizing the Synechocystis genes and proteins involved in tocopherol biosynthesis involved the expression and biochemical analysis of these genes in E. coli. The Synechocystis SLL0418 gene sequence was subcloned from pSLL0418-1 as a Nde1/Hind3 fragment into the Nde1 and Hind3 sites of the E. coli expression vector, pET30B. The resulting plasmid construct was designated p041798 and was transformed into the E. coli strain BL21(DE3)pLysS. Protein expression was induced with 1 mM isopropylthio-b-galactoside (IPTG) in the cells transformed with p041798 and cells transformed with the empty pET30B vector. Induced cultures were grown for 3 hours at 28° C. in a shaking incubator after which the cells were harvested by centrifugation at 8,000 g for 10 minutes at 4° C. and stored at 80° C. The cell pellets were resuspended in 50 mM Tris-HCl pH 8.0, 5 mM DTT, 1 mM PMSF and homogenized with four 10 second burst with a sonicator. Triton X 100 was then added to a final concentration of 1% and the mixture was incubated on ice for 30 minutes. The insoluble material was then removed by centrifugation at 40,000 g for 30 minutes and the supernatant was saved for methyltransferase assays.

Preparation of 2-Methyl-6-phytolplastoquinol Substrate

A mixture of 6 different isomers of methylphytylplastoquinone was synthesized as described by Henry et al. (1987) Biochem J 242: 367–373. Two hundred and fifty mg of the mixed methylphytylplastoquinone isomer preparation was suspended in ethylether. This mixture was oxidized by adding 100 mg of silver oxide and incubating the mixture for 2 hours at room temperature. The silver oxide was then removed by centrifugation and the methylphytylplastoquinone isomers were dried under nitrogen gas and resuspended in hexane. The 2-methyl-6-phytylplastoquinone was purified from this mixture of isomers on a 7.8×300 mm Waters mPorasil HPLC column. The compound was eluted isocraticly using a mobile phase consisting of 999:1 (vol/vol) hexane:dioxane. The fraction containing the purified 2-methyl-6-phytylplastoquinone was collected and dried under a stream of nitrogen gas. The 2-methyl-6-phytylplastoquinone was then resuspended in 1 mL of absolute ethanol in a silanized tube and reduced to 2-methyl-6-phytylplastoquinol by adding 50 μl of 50 mg/mL sodium borohydride. The mixture was incubated at room temperature for 5 minutes. The reaction was stopped by adding 200 μl of 0.1 M acetic acid and incubating the mixture for an additional 5 minutes at room temperature. The 2-methyl-6-phytylplastoquinol was then extracted by adding 300 μl of water and 1 mL of hexane. The hexane phase was collected, dried under nitrogen and resuspended in 100 μl of ethanol for use in methyltransferase assays.

Preparation of 2-Methyl-6-solanylplastoquinol Substrate

The 2-methyl-6-solanylplastoquinol substrate was purified from Iris bulbs. One hundred gm of iris bulbs were homogenized in 500 mL acetone. The homogenate was filtered through two layers of miracloth. Five hundred mL of petroleum ether was added to the filtrate. Water was then added until two phases formed. The lower phase (aqueous fraction) was discarded and the upper phase (organic fraction) was washed two times with water to remove any residual acetone. The organic fraction was then dried and resuspended in 10 mL of ethylether. Two hundred mg of silver oxide was then added and the mixture was incubated for 1 hour at room temperature. The silver oxide was then spun down and the supernatant was dried under nitrogen gas.

The resulting lipid residue was resuspended in hexane and fractionated on silica TLC plates developed in 20% ethylether 80% petroleum ether. A small portion of the TLC plate was sprayed with leucomethylene blue, as described in Crane and Barr (1971) Methods in Enzymology, 18:137–169, to detect the 2-methyl-6-solanylplastoquinone band. The 2-methyl-6-solanylplastoquinone band was then scraped from the plate and eluted from the silica with ethylether. The 2-methyl-6-solanylplastoquinone was dried under nitrogen and resuspended ethanol. The 2-methyl-6-solanylplastoquinone was then reduced and prepared for use in assays as described for the 2-methyl-6-phytylplastoquinone substrate.

In vitro 2-Methyl-6-phytylplastoquinol and 2-Methyl-6-solanylplastoquinol Methyltransferase Assays of E. coli Expressed SLL0418 Gene Extracts from *E. coli* expressing the SLL0418 gene were assayed for 2-methyl-6-phytylplastoquinol and 2-methyl-6-solanylplastoquinol methyltransferase activity. *E. coli* extracts (prepared as described above) were assayed in 1 mL reactions containing 50 mM Tris-HCl pH 8.0, 5 mM DTT, ~5 mM 2-methyl-6-phytylplastoquinol or 2-methyl-6-solanylplastoquinol (prepared as described above), and 1.7 uM [$^{14}$C-methyl]-S-adenosylmethionine (58 mCi/mmol). The reactions were incubated at room temperature for 30 minutes. Four and one half mL of 2:1 (vol:vol) CHCl$_3$:methanol and 2 mL 0.9% NaCl was then added and each tube was mixed thoroughly. Phases were separated by centrifugation and the lower CHCl$_3$ phase was transferred to a new tube. A small amount of silver oxide was then added to the CHCl$_3$ phase, after which the CHCl$_3$ was evaporated under a stream of air. The dried residue was then resuspended in hexane and spotted onto a silica TLC plate. The TLC plate was developed in 7:3 (vol:vol) petroleum ether-:ethylether and exposed to film overnight. TLC fractions corresponding to radiolabeled compounds with the correct R$_f$ value for either plastoquinone of 2,3-dimethylphytylplastoquinone were scraped from the TLC plate and subjected to scintillation counting. The results of these assays showed that the *E. coli* expressed SLL0418 was able to methylate both 2-methyl-6-phytylplastoquinol or 2-methyl-6-solanylplastoquinol to form 2,3-dimethylphytlyplastoquinol and 2,3-dimethylsolanylplastoquinol respectively as shown in Table 1 below. Extracts isolated from *E. coli* transformed with the empty vector control were unable to methylate either substrate.

TABLE 1

Biochemical analysis of SLL0418 protein expressed in *E. coli*.

| | substrate | |
|---|---|---|
| | 2-methyl-6-phytylplastoquinol | 2-methyl-6-solanylplastoquinol |
| SLL0418 | 484 CPM | 174 CPM |
| Empty Vector Control | 25 CPM | 26 CPM |

For the work summarized in this Table 1, extracts from *E. coli* cells transformed with an empty vector control (pET30B) and the SLL0418 expression construct were assayed for their ability to methylate 2-methyl-6-phytylplastoquinol and 2-methyl-6-solanylplastoquinol. Assays were performed as described. The values in the table represent the amount of $^{14}$C labeled 2,3-dimethyl-6-phytylplastoquinol and 2,3-dimethylsolanylplastoquinol products produced from reactions in which 2-methyl-6-phytylplastoquinol and 2-methyl-6-solanylplastoquinol were respectively used as substrates. While significant amounts of radioactivity above background levels were incorporated into the 2,3-dimethyl-6-phytylplastoquinol and 2,3-dimethyl-6-solanylplastoquinol products in assay using extracts from cells expressing the SLL0418 gene, no significant incorporation into these two products was observed in assays using extracts from control cells.

Qualitative Manipulation of Tocopherols in Arabidopsis and Other Plants by Overexpressing the Synechocystis 2-Methyl-6-phytylplastoquinol/2-Methyl-6-solanylplastoquinol-9 methyltransferase From the genetic and biochemical studies described above, it is demonstrated that SLL0418 encodes the Synechocystis 2-methyl-6-phytylplastoquinol/2-methyl-6-solanylplastoquinol-9 methyltransferase, the first methyltransferase enzyme in the synthesis of tocopherols and plastoquinone in photosynthetic organisms. The Synechocystis 2-methyl- 6-phytylplastoquinol/2-methyl-6-solanylplastoquinol-9 methyltransferase can be used to directly alter the levels of α-, δ-, γ- and β-tocopherol in plant tissues by overexpressing the activity in the desired plant tissues. We chose Arabidopsis as model plant systems to demonstrate the effect in plant tissues of overexpressing SLL0418 and plant homologs in different plant tissues. Arabidopsis was selected due to its ease of transformation by vacuum infiltration and subsequent molecular and genetic analysis of transformants are routine and well-established. However, it is important to stress that Arabidopsis tocopherol profiles in leaf and seeds are similar to those in a large number of agricultural crops and demonstrating the modification of Arabidopsis tocopherol profiles by expressing the Synechocystis γ-tocopherol methyltransferase in these tissues will be similar to results that will occur in any agricultural crop.

Figure 5:
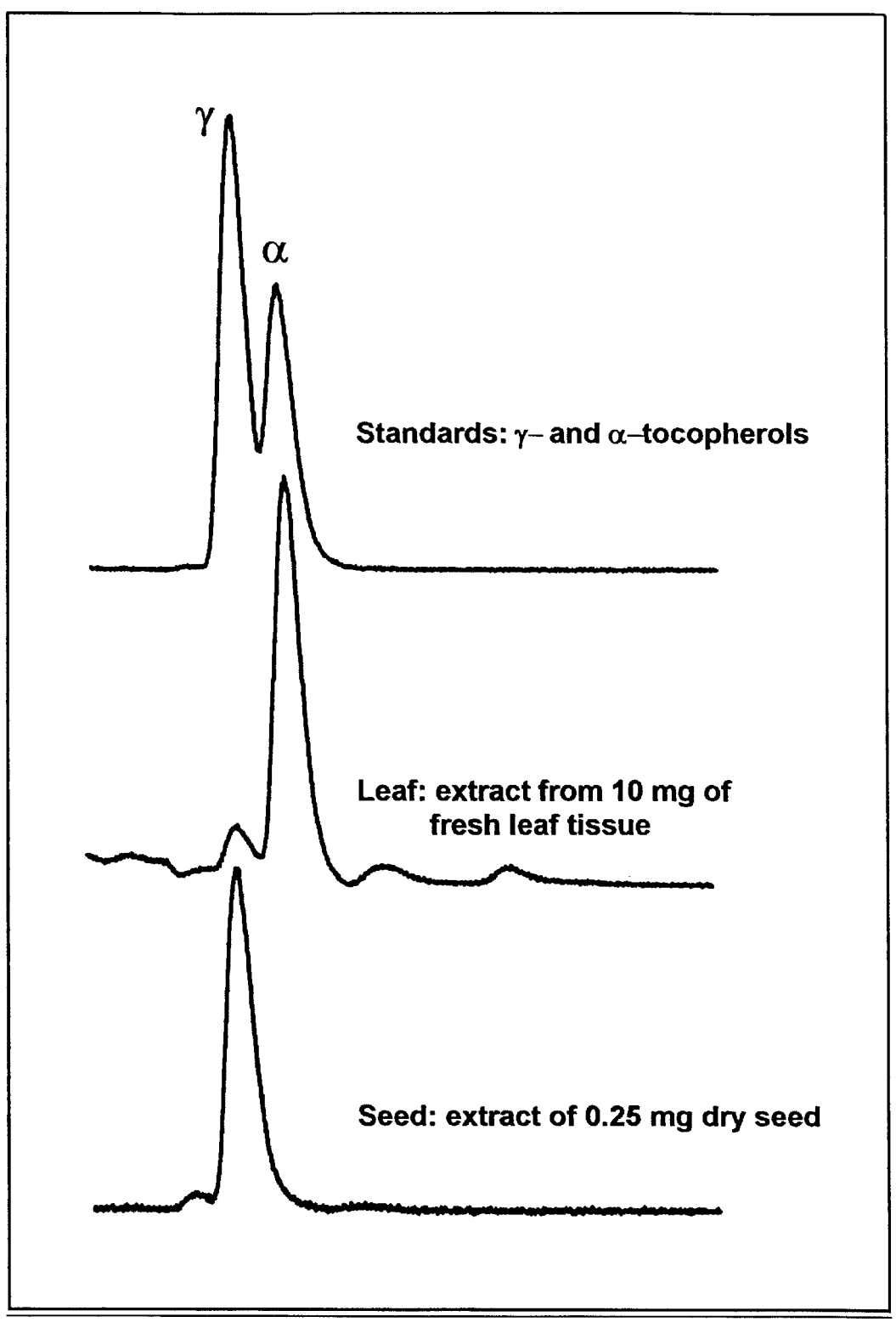
FIG. 5 illustrates a qualitative analysis of tocopherols in Arabidopsis tissues and their relative abundance.

Tocopherol analysis of Arabidopsis tissues by HPLC (FIG. 5 and Table 2) show that Arabidopsis seeds possess relatively simple tocopherol profiles with seeds containing 95% γ-tocopherol and 5% δ-tocopherol. These simple tocopherol profiles make these Arabidopsis seed an ideal target in which to demonstrate the functional consequences of expressing SLL0418 in plants. From a qualitative perspective, increasing 2-methyl-6-phytylplastoquinol/2-methyl-6-solanylplastoquinol-9 methyltransferase gene expression in Arabidopsis seeds will result in increased seed γ-tocopherol levels as a proportion of total tocopherols, that is the conversion of δ-tocopherol to γ-tocopherol, approaching 100%. Modification of 2-methyl-6-phytylplastoquinol/2-methyl-6-solanylplastoquinol-9 methyltransferase activity in plants by molecular techniques using SLL0418 can therefore be used to positively affect the production of γ-tocopherol from δ-tocopherol and α-tocopherol from β-tocopherol. Constitutive overexpression of SLL0418 may be done utilizing the CaMV 35S promoter and three different SLL0418 constructs: 1) SLL0418 without targeting sequences, 2) SLL0418 with the targeting sequence for the Arabidopsis γ-tocopherol methyltransferase gene and 3) SLL0418 with the rubisco small subunit targeting sequence which would direct it to the stroma. The consequences of this altered expression on tocopherol, plastoquinone and carotenoid levels and profiles in various plant tissues may be determined as described below. If needed, seed specific promoters can be used to maximize and restrict expression in seeds.

Multiple independent transformants may be produced for each construct, confirmed by southern analysis, characterized at the mRNA level and their effects on individual chloroplastic components of interest analyzed. The integration and gene copy number of each chimeric gene in each line may be confirmed by southern analysis, the level of SLL0418 mRNA may be determined by Northern blot analysis, and 2-methyl-6-phytylplastoquinol/2-methyl-6-solanylplastoquinol-9 methyltransferase activity determined following methods described in (22). Analysis of tocopherols, plastoquinones and carotenoids may be by a combination of HPLC, optical and mass spectra as described. Analysis of tocopherol levels is performed by HPLC with fluorescence detection using known standards and standard curves and when needed by LC or GC:mass spectroscopy. In MS analysis the absolute level of tocopherol is quantified by isotopic dilution with a known, "heavy carbon" tocopherol standard added at the start the extraction. Determination based on fresh weight of tissue or relative to chlorophyll a is also performed. Total carotenoid levels are determined spectrophotometrically and the levels of individual carotenes quantified by C18 HPLC and optical spectra quantified to standards. In the course of these experiments high expressing lines with simple insertions that segregate as single genetic loci in progeny are identified.

Isolation and Functional Testing of SLL0418 Plant Homologs.

Having defined SLL0418 as a 2-methyl-6-phytylplastoquinol/2-methyl-6-solanylplastoquinol-9 methyltransferase provides several tools for isolation of plant homologs. First, the SLL0418 DNA sequence is used as a probe to isolate plant homologs by homology. Second, the SLL0418 DNA and protein sequence may be used to screen public or private computer databases of plant cDNAs (dbEST databases) and genomic sequences. Once promising candidates are identified they are functionally tested by antisense inhibition or overexpression in Arabidopsis and by functional complementation of the Synechocystis SLL0418 knockout mutant described above. Alternatively, the genes can be expressed in E. coli and the protein assayed directly using the appropriate substrate. In this later case, if the plant cDNA were a functional homology of SLL0418 expression of the cDNA in the SLL0418 knockout mutant would restore α-tocopherol production to the knockout mutant. The knockout mutant may also be used to directly select for plant homologs by functional complementation if a selectable phenotype is observed for the knockout mutant. Once plant homologs are identified they are used to directly modify tocopherol production of the host plant or other plants as described above for SLL0418.

Plant homologs to SLL0418 are isolated by techniques well known in the art including the screening of plant genomic or cDNA libraries with a probe comprising at least part of the sequence of SEQ ID NO:1. Plant cDNA libraries are custom made using procedures available in the art, such as those disclosed by Sambrook et al (34). Or premade cDNA libraries are screened such as those available form Stratagene.

The screening of cDNA or genomic libraries with a probe comprising at least part of the sequence of SEQ ID NO:1 may be done using stringent hybridization conditions. Stringent conditions are sequence dependent and are different in different circumstances. Generally, stringent conditions are selected to be about 5° C. lower than the normal thermal melting point (Tm) for the specific sequence at a defined ionic strength and pH. The Tm is the temperature (under defined ionic strength and pH) at which 50% of target sequence hybridizes to a perfectly matched probe. Typically, stringent conditions involve washing at 65° C. with 0.2× SSC. An alternative approach is to amplify the plant homolog by PCR using procedures readily available in the art, such as those disclosed by Innis et al. which is hereby incorporated by reference in its entirety.

TABLE 2

Tocopherol Levels and Composition in Selected Crops and Plant Oils (2, 19) and expected changes with SLL0418 overexpressed

| Crop Species (tissue) | Tocopherol composition of untransformed plant | Expected tocopherol composition of transgenic plants with SLL0418 over-expressed |
|---|---|---|
| Soybean[1] (seed/oil) | 70% γ-tocopherol<br>22% δ-tocopherol<br>7% α-tocopherol<br>1% β-tocopherol | 8% α-tocopherol<br>92% γ-tocopherol |
| Oil Palm[1] (seed oil) | 25% α-tocopherol<br>30% α-tocotrienol<br>40% γ-tocotrienol<br>5% δ-tocotrienol | 25% α-tocopherol<br>30% α-tocotrienol<br>45% γ-tocotrienol |
| Peanut[2] (raw nut) | 50% α-tocopherol<br>50% γ-tocopherol | 50% α-tocopherol<br>50% γ-tocopherol |
| Peanut[2] (nut oil) | 33% α-tocopherol<br>66% γ-tocopherol | 33% α-tocopherol<br>66% γ-tocopherol |
| safflower[2] (seed oil) | 48% α-tocopherol<br>22% γ-tocopherol<br>30% δ-tocopherol | 48% α-tocopherol<br>52% γ-tocopherol |
| rapeseed[2] (seed oil) | 25% α-tocopherol<br>75% γ-tocopherol | 25% α-tocopherol<br>75% γ-tocopherol |
| cotton seed[1] (seed oil) | 40% α-tocopherol<br>58% γ-tocopherol<br>2% δ-tocopherol | 40% α-tocopherol<br>60% γ-tocopherol |
| wheat[2] (whole wheat flour) | 20% α-tocopherol<br>7% α-tocotrienol<br>17% β-tocopherol<br>56% β-tocotrienol | 37% α-tocopherol<br>63% α-tocotrienol |
| wheat[1] (germ oil) | 75% α-tocopherol<br>25% γ-tocopherol | 75% α-tocopherol<br>25% γ-tocopherol |
| corn[1] (oil) | 22% α-tocopherol<br>68% γ-tocopherol<br>3% β-tocopherol<br>7% δ-tocopherol | 25% α-tocopherol<br>75% γ-tocopherol |
| castor bean[2] (oil) | 50% γ-tocopherol<br>50% δ-tocopherol | 100% γ-tocopherol |
| corn[2] (whole grain) | 11% α-tocopherol<br>69% γ-tocopherol<br>4% α-tocotrienol<br>9% γ-tocotrienol<br>7% β-tocotrienol | 11% α-tocopherol<br>69% γ-tocopherol<br>11% α-tocotrienol<br>9% γ-tocotrienol |
| barley[2] (whole grain) | 14% α-tocopherol<br>2% γ-tocopherol<br>10% β-tocopherol<br>44% α-tocotrienol<br>7% γ-tocotrienol<br>23% β-tocotrienol | 24% α-tocopherol<br>2% γ-tocopherol<br>67% α-tocotrienol<br>7% γ-tocotrienol |
| rice[2] (whole grain) | 50% α-tocopherol<br>50% γ-tocopherol | 50% α-tocopherol<br>50% γ-tocopherol |
| potato[2] (tuber) | 95% α-tocopherol<br>5% γ-tocopherol | 95% α-tocopherol<br>5% γ-tocopherol |
| sunflower[2] (seeds raw) | 95% α-tocopherol<br>5% γ-tocopherol | 95% α-tocopherol<br>5% γ-tocopherol |
| sunflower[1] (seed oil) | 96% α-tocopherol<br>2% γ-tocopherol<br>2% β-tocopherol | 98% α-tocopherol<br>2% γ-tocopherol |
| banana[1] (fruit) | 100% α-tocopherol | 100% α-tocopherol |
| lettuce[1] (leaf) | 53% α-tocopherol<br>47% γ-tocopherol | 53% α-tocopherol<br>47% γ-tocopherol |
| broccoli[2] | 72% α-tocopherol<br>28% γ-tocopherol | 72% α-tocopherol<br>28% γ-tocopherol |
| cauliflower[3] | 44% α-tocopherol<br>66% γ-tocopherol | 44% α-tocopherol<br>66% γ-tocopherol |

TABLE 2-continued

Tocopherol Levels and Composition in Selected Crops and Plant Oils (2, 19) and expected changes with SLL0418 overexpressed

| Crop Species (tissue) | Tocopherol composition of untransformed plant | Expected tocopherol composition of transgenic plants with SLL0418 over-expressed |
|---|---|---|
| apple[2] | 100% α-tocopherol | 100% α-tocopherol |
| pears[2] | 93% α-tocopherol | 93% α-tocopherol |
|  | 7% γ-tocopherol | 7% γ-tocopherol |
| carrots[2] | 94% α-tocopherol | 94% α-tocopherol |
|  | 4% γ-tocopherol | 6% γ-tocopherol |
|  | 2% δ-tocopherol |  |

[1]McLaughlin PJ, Weihrauch JC (1979) Vitamin E content of foods. J Am Diet Ass 75: 647–665.
[2]Bauernfeind J (1980) Tocopherols in foods. In Vitamin E: A Comprehensive Treatise. L J Machlin ed., Marcel Dekker, Inc., New York pp. 99–168.

REFERENCES

The following references are incorporated by reference in their entirety.
1. Liebler, D. C., The role of metabolism in the antioxidant function of vitamin E. Critical Reviews in Toxicology, 1993. 23(2): p. 147–169.
2. Hess, J. L., Vitamin E, α-tocopherol, in *Antioxidants in Higher Plants*, R. Alscher and J. Hess, Editors. 1993, CRC Press: Boca Raton. p. 111–134.
3. Lichtenthaler, H., Planta, 1968. 81: p. 140–152.
4. Evans, H. and K. Bishop, On the existence of a hitherto unrecognized dietary factor essential for reproduction. Science, 1922. 56: p. 650–651.
5. Traber, M. G. and H. Sies, Vitamin E in humans: Demand and delivery. Annu. Rev. Nutr., 1996. 16: p. 321–347.
6. McLaughlin, P. and W. J C, Vitamin E content of foods. J. Am. Diet. Ass., 1979. 75: p. 647–665.
7. Peterson, D., Oat tocols: concentration and stability in oat products and distribution within kernels. Cereal-Chem, 1995. 72(1): p. 21–24.
8. Ball, G., *Fat-soluble vitamin assays in food analysis. A comprehensive review*. 1988, London: Elsevier Science Publishers LTD.
9. Sante, V. and A. Lacourt, The effect of dietary alpha-tocopherol supplementation and antioxidant spraying on colour stability and lipid oxidation of turkey meat. J. Sci. Food Agric., 1994. 65(4): p. 503–507.
10. Buckley, D., P. Morrissey, and J. Gray, Influence of dietary vitamin E on the oxidative stability and quality of pig meat. Journal of Animal Science, 1995. 73: p. 3122–3130.
11. Soll, J., α-*tocopherol and plastoquinone synthesis in chloroplast membranes*, in *Plant Cell Membranes*, L. Packer and R. Douce, Editors. 1987, Academic Press: San Diego. p. 383–392.
12. Parker, R., et al., Tocotrienols regulate cholesterol production in mammalian cells by post-transcriptional suppression of 3-hydroxy-3-methylglutaryl-coenzyme A reductase. J Biol Chem, 1993. 268(15): p. 11230–11238.
13. Kamal-Eldin, A. and L.-A. Appelqvist, The chemistry and antioxidant properties of tocopherols and tocotrienols. Lipids (Review), 1996. 31(7): p. 671–701.
14. Erin, A., V. Skrypin, and V. Kagan, Formation of α-tocopherol complexes with fatty acids. Biochim. Biophys. Acta, 1985. 815: p. 209.
15. Kagan, V., Tocopherol stabilizes membrane against phospholipase A, fatty acids, and lysophospholipids., in Vitamin E: Biochemistry and Health Implications., A. Diplock, et al., Editors. 1989, Ann. N.Y. Acad. Sci.: p. 121.
16. Gomez-Fernandes, J., et al., Localization of α-tocopherol in membranes., in *Vitamin E. Biochemistry and Health Implications.*, A. Diplock, et al., Editors. 1989, Ann. N.Y. Acad. Sci.: p. 109.
17. Fukuzawa, K., et al., Antioxidant activities of tocopherols on iron(2+)-ascorbate-induced lipid peroxidation in lectithin liposomes. Lipids, 1982. 17: p. 511–513.
18. Fryer, M. J., The antioxidant effects of thylakoid vitamin E (alpha-tocopherol). Plant Cell Environ, 1992. 15(4): p. 381–392.
19. Taylor, P. and P. Barnes, Analysis of vitamin E in edible oils by high performance liquid chromatography. Chemy Ind., 1981. (17th October): p. 722–726.
20. Soll, J. and G. Schultz, 2-methyl-6-phytylquinol and 2,3-dimethyl-5-phytylquinol as precursors of tocopherol synthesis in spinach chloroplasts. Phytochemistry, 1980. 19(2): p. 215–218.
21. Cook, W. B. and D. Miles, Nuclear mutations affecting plastoquinone accumulation in maize. Photosynthesis Research, 1992. 31: p. 99–111.
22. D' Harlingue A and B. Camara, Plastid enzymes of terpenoid biosynthesis: purification and characterization of a gamma-tocopherol methyltransferase. J. Biol. Chem., 1985. 260(68): p. 15200–15203.
23. Ishiko, H., et al., Some properties of gamma-tocopherol methyltransferase solubilized from spinach chloroplast. Phytochemistry, 1992. 31(5): p. 1499–1500.
24. Demurin, Y., Genetic varibility of tocopherol composition in sunflower seeds. Helia, 1993. 16: p. 59–62.
25. Skoric, D., Y. Demurin, and J. Sinisa. Development of hybrids with various oil quality in Proceedings of 14th International Sunflower Conference. 1996. Beijing/Shenyang, China:
26. Golden, S., Mutagenesis of cyanobacteria by classical and gene-transfer-based methods. Methods in Enzymology, 1988. 167: p. 714–727.
27. Kaneko, T., Sato, S., Kotani, H., Tanaka, A., Asamizu, E., Nakamura, Y., Miyajima, N., Hirosawa, M., Sugiura, M., Sasamoto, S., Kimura, T., Hosouchi, T., Matsuno, A., Muraki, A., Nakazaki, N., Naruo, K., Okumura, S., Shimpo, S., Takeuchi, C., Wada, T., Watanabe, A., Sequence analysis of the genome of the unicellular Cyanobacterium Synechocystis sp. strain PCC6803. II. Sequence determination of the entire genome and assignment of potential protein-coding regions. DNA Res., 1996. 3: p. 109–136.
28. Porter, R., DNA transformations. Methods in Enzymology, 1988. 167: p. 703–712.
29. Williams, J., Construction of specific mutations in photosystem II photosynthetic reaction center by genetic engineering methods in Synechocystis 6803. Methods in Enzymology, 1988. 167: p. 766–777.
30. Harlow and Lane, Antibodies: a laboratory manual, Cold Spring Harbor Pubs., N.Y. (1988).
31. Ausbel et al., Current Protocols in Molecular Biology, Greene Publishing and Wiley-Interscience, N.Y. (1987)
32. Innis, M. et al., PCR Protocols: a guide to methods and applications, Academic Press, San Diego (1990).
33. Scopes, Protein Purification: Principles and Practice, Springer-Verlag, N.Y. (1982).
34. Sambrook et al., Molecular Cloning: A laboratory manual (2nd edition), Vol. 1–3. Cold Spring Harbor Laboratory (1989).

We claim:

1. A gene construct comprising a 2-methyl-6-phytylplastoquinol/2-methyl-6-solanylplastoquinol-9 methyltransferase coding sequence from Synechocystis and a plant active promoter, the coding sequence being under the control of the promoter, the coding sequence and the promoter not natively associated with each other.

2. A gene construct comprising a 2-methyl-6-phytylplastoquinol/2-methyl-6-solanylplastoquinol-9 methyltransferase coding sequence and a plant active promoter, the coding sequence being under the control of the promoter, the coding sequence and the promoter not natively associated with each other, wherein the 2-methyl-6-phytylplastoquinol/2-methyl-6-solanylplastoquinol-9 methyltransferase coding sequence is SEQ ID NO:1.

3. A transgenic plant comprising in its genome the gene construct of claim 1.

4. The seed of the plant of claim 3.

5. A transgenic plant of a species which natively produces δ-tocopherol, the tocopherol profile of the transgenic plant differing from non-transgenic plants of that species by the production of γ-tocopherol in place of the δ-tocopherol, the transgenic plant comprising in its genome a gene construct comprising a coding sequence for a 2-methyl-6-phytylplastoquinol/2-methyl-6-solanylplastoquinol-9 methyltransferase from Synecocystis operably linked to a plant active promoter.

6. Seeds of the plant of claim 5.

7. A transgenic plant as claimed in claim 5 wherein the 2-methyl-6-phytylplastoquinol/2-methyl-6-solanylplastoquinol-9 methyltransferase gene is SEQ ID NO:1.

* * * * *

SEQUENCE LISTING

<160> NUMBER OF SEQ ID NOS: 4

<210> SEQ ID NO 1
<211> LENGTH: 957
<212> TYPE: DNA
<213> ORGANISM: Synechocystis PCC6803
<220> FEATURE:
<221> NAME/KEY: CDS
<222> LOCATION: (1)..(954)

<400> SEQUENCE: 1

```
atg ccc gag tat ttg ctt ctg ccc gct ggc cta att tcc ctc tcc ctg      48
Met Pro Glu Tyr Leu Leu Leu Pro Ala Gly Leu Ile Ser Leu Ser Leu
 1               5                  10                  15 gcg atc gcc gct gga ctg tat ctc cta act gcc cgg ggc tat cag tca      96
Ala Ile Ala Ala Gly Leu Tyr Leu Leu Thr Ala Arg Gly Tyr Gln Ser
            20                  25                  30 tcg gat tcc gtg gcc aac gcc tac gac caa tgg aca gag gac ggc att     144
Ser Asp Ser Val Ala Asn Ala Tyr Asp Gln Trp Thr Glu Asp Gly Ile
        35                  40                  45 ttg gaa tat tac tgg ggc gac cat atc cac ctc ggc cat tat ggc gat     192
Leu Glu Tyr Tyr Trp Gly Asp His Ile His Leu Gly His Tyr Gly Asp
    50                  55                  60 ccg cca gtg gcc aag gat ttc atc caa tcg aaa att gat ttt gtc cat     240
Pro Pro Val Ala Lys Asp Phe Ile Gln Ser Lys Ile Asp Phe Val His
65                  70                  75                  80 gcc atg gcc cag tgg ggc gga tta gat aca ctt ccc ccc ggc aca acg     288
Ala Met Ala Gln Trp Gly Gly Leu Asp Thr Leu Pro Pro Gly Thr Thr
                85                  90                  95 gta ttg gat gtg ggt tgc ggc att ggc ggt agc agt cgc att ctc gcc     336
Val Leu Asp Val Gly Cys Gly Ile Gly Gly Ser Ser Arg Ile Leu Ala
            100                 105                 110 aaa gat tat ggt ttt aac gtt acc ggc atc acc att agt ccc caa cag     384
Lys Asp Tyr Gly Phe Asn Val Thr Gly Ile Thr Ile Ser Pro Gln Gln
        115                 120                 125 gtg aaa cgg gcg acg gaa tta act cct ccc gat gtg acg gcc aag ttt     432
Val Lys Arg Ala Thr Glu Leu Thr Pro Pro Asp Val Thr Ala Lys Phe
    130                 135                 140 gcg gtg gac gat gct atg gct ttg tct ttt cct gac ggt agt ttc gac     480
Ala Val Asp Asp Ala Met Ala Leu Ser Phe Pro Asp Gly Ser Phe Asp
145                 150                 155                 160 gta gtt tgg tcg gtg gaa gca ggg ccc cac atg cct gac aaa gct gtg     528
Val Val Trp Ser Val Glu Ala Gly Pro His Met Pro Asp Lys Ala Val
                165                 170                 175 ttt gcc aag gaa tta ctg cgg gtc gtg aaa cca ggg ggc att ctg gtg     576
Phe Ala Lys Glu Leu Leu Arg Val Val Lys Pro Gly Gly Ile Leu Val
            180                 185                 190 gtg gcg gat tgg aat caa cgg gac gat cgc caa gtg ccc ctc aac ttc     624
Val Ala Asp Trp Asn Gln Arg Asp Asp Arg Gln Val Pro Leu Asn Phe
        195                 200                 205 tgg gaa aaa cca gtg atg cga caa ctg ttg gat caa tgg tcc cac cct     672
Trp Glu Lys Pro Val Met Arg Gln Leu Leu Asp Gln Trp Ser His Pro
    210                 215                 220 gcc ttt gcc agc att gaa ggt ttt gcg gaa aat ttg gaa gcc acg ggt     720
Ala Phe Ala Ser Ile Glu Gly Phe Ala Glu Asn Leu Glu Ala Thr Gly
225                 230                 235                 240 ttg gtg gag ggc cag gtg act act gct gat tgg act gta ccg acc ctc     768
Leu Val Glu Gly Gln Val Thr Thr Ala Asp Trp Thr Val Pro Thr Leu
                245                 250                 255
```

```
ccc gct tgg ttg gat acc att tgg cag ggc att atc cgg ccc cag ggc    816
Pro Ala Trp Leu Asp Thr Ile Trp Gln Gly Ile Ile Arg Pro Gln Gly
        260                 265                 270 tgg tta caa tac ggc att cgt ggg ttt atc aaa tcc gtg cgg gaa gta    864
Trp Leu Gln Tyr Gly Ile Arg Gly Phe Ile Lys Ser Val Arg Glu Val
        275                 280                 285 ccg act att tta ttg atg cgc ctt gcc ttt ggg gta gga ctt tgt cgc    912
Pro Thr Ile Leu Leu Met Arg Leu Ala Phe Gly Val Gly Leu Cys Arg
        290                 295                 300 ttc ggt atg ttc aaa gca gtg cga aaa aac gcc act caa gct taa        957
Phe Gly Met Phe Lys Ala Val Arg Lys Asn Ala Thr Gln Ala
305                 310                 315
```

<210> SEQ ID NO 2
<211> LENGTH: 318
<212> TYPE: PRT
<213> ORGANISM: Synechocystis PCC6803

<400> SEQUENCE: 2

```
Met Pro Glu Tyr Leu Leu Pro Ala Gly Leu Ile Ser Leu Ser Leu
 1               5                  10                  15

Ala Ile Ala Ala Gly Leu Tyr Leu Leu Thr Ala Arg Gly Tyr Gln Ser
                20                  25                  30

Ser Asp Ser Val Ala Asn Ala Tyr Asp Gln Trp Thr Glu Asp Gly Ile
         35                  40                  45

Leu Glu Tyr Tyr Trp Gly Asp His Ile His Leu Gly His Tyr Gly Asp
     50                  55                  60

Pro Pro Val Ala Lys Asp Phe Ile Gln Ser Lys Ile Asp Phe Val His
 65                  70                  75                  80

Ala Met Ala Gln Trp Gly Gly Leu Asp Thr Leu Pro Pro Gly Thr Thr
                 85                  90                  95

Val Leu Asp Val Gly Cys Gly Ile Gly Gly Ser Ser Arg Ile Leu Ala
                100                 105                 110

Lys Asp Tyr Gly Phe Asn Val Thr Gly Ile Thr Ile Ser Pro Gln Gln
            115                 120                 125

Val Lys Arg Ala Thr Glu Leu Thr Pro Pro Asp Val Thr Ala Lys Phe
        130                 135                 140

Ala Val Asp Asp Ala Met Ala Leu Ser Phe Pro Asp Gly Ser Phe Asp
145                 150                 155                 160

Val Val Trp Ser Val Glu Ala Gly Pro His Met Pro Asp Lys Ala Val
                165                 170                 175

Phe Ala Lys Glu Leu Leu Arg Val Val Lys Pro Gly Gly Ile Leu Val
            180                 185                 190

Val Ala Asp Trp Asn Gln Arg Asp Asp Arg Gln Val Pro Leu Asn Phe
        195                 200                 205

Trp Glu Lys Pro Val Met Arg Gln Leu Leu Asp Gln Trp Ser His Pro
    210                 215                 220

Ala Phe Ala Ser Ile Glu Gly Phe Ala Glu Asn Leu Glu Ala Thr Gly
225                 230                 235                 240

Leu Val Glu Gly Gln Val Thr Thr Ala Asp Trp Thr Val Pro Thr Leu
                245                 250                 255

Pro Ala Trp Leu Asp Thr Ile Trp Gln Gly Ile Ile Arg Pro Gln Gly
            260                 265                 270

Trp Leu Gln Tyr Gly Ile Arg Gly Phe Ile Lys Ser Val Arg Glu Val
        275                 280                 285

Pro Thr Ile Leu Leu Met Arg Leu Ala Phe Gly Val Gly Leu Cys Arg
```

```
              290                 295                 300
Phe Gly Met Phe Lys Ala Val Arg Lys Asn Ala Thr Gln Ala
305                 310                 315

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: sense-
      strand specific primer SLL0418F

<400> SEQUENCE: 3
catatgcccg agtatttgct tctg                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      non-sense-strand specific primer SLL0418R

<400> SEQUENCE: 4
tttaagcttg agtggcgttt tttc                                          24
```